United States Patent [19]

Parisheva

[11] Patent Number: 4,495,171

[45] Date of Patent: Jan. 22, 1985

[54] PREPARATION FOR TREATING GUM DISEASE

[76] Inventor: Snejana G. Parisheva, 15 Vicora Linkway, Don Mills, Ontario, Canada

[21] Appl. No.: 591,905

[22] Filed: Mar. 22, 1984

Related U.S. Application Data

[63] Continuation-in-part of Ser. No. 438,208, Nov. 1, 1982, abandoned.

[51] Int. Cl.$^3$ .................... A61K 7/26; A61K 35/78
[52] U.S. Cl. .................................. 424/58; 424/195.1
[58] Field of Search ............................. 424/195

[56] References Cited

U.S. PATENT DOCUMENTS

| 30,834 | 12/1860 | Popp | 424/58 |
| 137,542 | 4/1873 | Gahn | 424/58 |
| 1,073,725 | 9/1913 | Yeganian | 424/153 |
| 1,558,160 | 10/1925 | Gearhart | 424/154 |
| 2,010,910 | 8/1935 | Atkins | 424/49 |

OTHER PUBLICATIONS

Poffer's Cyclopedia, p. 94, 1950.

*Primary Examiner*—Jerome D. Goldberg
*Assistant Examiner*—John W. Rollins, Jr.
*Attorney, Agent, or Firm*—Ridout & Maybee

[57] ABSTRACT

A preparation comprising a mixture of dry alum powder and dry powdered cloves have been found to be effective for the treatment of gum diseases.

7 Claims, No Drawings

PREPARATION FOR TREATING GUM DISEASE

This application is a continuation-in-part of application Ser. No. 438,208, filed on Nov. 1, 1982, now abandoned.

The present invention relates to a preparation for the treatment of diseased gums, and a method of treating diseased gums by use of said preparation.

There are a number of gum diseases which may be effectively treated by the use of the present preparation. The most dramatic results have been achieved with regard to the treatment of swollen gums, bleeding gums, and sensitive gums, however the present preparation is also effective for the treatment of shrunken or receding gums, and pyorrhea.

The preparation of the present invention comprises a mixture of dry powdered alum and dry powdered cloves. The use of alum as an astringent in dentifrice, mouthwash and other preparations for the mouth, teeth or gums has been known. Also, the use of cloves, generally in the form of oil of cloves, as a flavoring agent for dentifrice, mouthwash and other preparations for the mouth, teeth or gums is well known. However, the unique properties of a mixture of dry alum and dry cloves in powdered form in accordance with the present invention was hitherto unknown in the art relating to preparations for treating gum disease.

While beneficial results can be obtained by using a mixture of alum and clove powder mixed in various proportions to treat the gums, it has been found that a particular formulation affords a general treatment for gum disease and is thus preferred. Accordingly, without limiting the scope of the present invention, a preferred embodiment of the present invention will hereafter be described.

The term "alum" as used herein refers to the chemical compound by that designation commonly available in commerce in the United States and Canada. Alum so referred to is accepted in the trade as comprising a solid double sulfate containing aluminum and is commonly available in grocery or drug stores as aluminum potassium sulfate ($AlK(SO_4)_2$) or aluminum ammonium sulfate ($AlNH_4(SO_4)_2$). However, other alum compounds may be used in accordance with the present invention. Likewise, the term "cloves" as used herein refers to the spice in whole form which may be purchased at most grocery stores in the United States or Canada. Cloves are actually the unexpanded flower buds of the plant *Eugenia caryophyllus*.

Prior to mixing the ingredients of the preparation, it is preferable to dry them thoroughly. Thus, drug quality alum and whole cloves of the kind obtainable at a grocery store are dried for 8 to 10 hours at a temperature of 180° to 200° F. Upon cooling to room temperature the alum and the cloves are each ground or crushed to a powder prior to mixing. The preferred formulation of the preparation of the invention requires that the dry powdered alum and the dry powdered cloves be mixed in approximately equal proportions by volume.

It has been found that the combined healing properties of the alum and cloves is most effective for the treatment of gum disease generally when such equal proportions are mixed to formulate the present preparation. It is felt that the powdered cloves constitute the primary healing agent as this form of cloves provides a burning sensation when applied to the gums. The powdered alum component of the preparation counteracts the burning effect of the cloves by causing the mouth to water due to the strong astringency of alum in this form. When both ingredients are present in approximately equal proportions by volume, the burning effect of the cloves is counteracted by the astringent property of the alum so that maximum benefit of both ingredients is obtained for the treatment of gum disease. Additionally, the preparation disinfects diseased portions of the gums to which it is applied by virtue of the strong antiseptic properties of the combination of dry alum and cloves.

The preferred method of treatment is to apply the dry powdered preparation directly onto the diseased gums and then to allow the mouth to drain for 1 or 2 minutes before rinsing the gums with fresh water. By performing this treatment 2 or 3 times a day, swollen gums usually return to normal size and firmness in 2 or 3 days. Bleeding gums or sensitive gums are also rendered normal upon treatment in this manner for 2 or 3 days, whereas pyorrhea requires about one week of daily treatments to effect healing. Once the gums have returned to normal further treatment is not necessary. Where shrunken gums are treated using the present preparation, the method of treatment set out above must be continued for 2 or 3 months as this length of time is needed to allow the gums to regenerate.

While it is preferred to dry the cloves and alum as aforesaid, the cloves may be dried in as little as 4 to 6 hours by raising the drying temperature to 250° F. Dry alum is fairly hygroscopic and thus, the preparation must be tightly sealed against moisture when being stored.

As stated above, it has been found that the preferred preparation for the general treatment of gum disease is obtained by mixing equal volumes of dry alum and dry cloves in powdered form. However, beneficial results can be obtained from using a preparation comprising from 1 to 9 parts of alum by volume with from 9 to 1 parts respectively of cloves by volume. In fact the optimal composition of the preparation usually varies according to the disease and the sensitivity of the gums being treated. It has only been through the experience of clinical trials that the preferred preparation has been determined to be generally effective against the broad spectrum of gum disorders aforementioned.

Similarly, while the preferred method of treatment involves 2 or 3 applications of the preparation daily, benefits can be derived from as little as a single daily treatment. However, in order to achieve significant regeneration of shrunken gums, daily treatments performed 2 or 3 times must be maintained.

I claim:

1. A preparation for treating pyorrhea and other gum diseases which result in symptoms of swollen, bleeding, sensitive, shrunken or receding gums, comprising a mixture of from 10 to 90 percent by volume dry powdered alum and from 90 to 10 percent by volume dry powdered cloves.

2. A preparation as claimed in claim 1, wherein the alum and cloves are mixed in approximately equal proportions by volume.

3. A method for treating pyorrhea and other gum diseases which result in symptoms of swollen, bleeding, sensitive, shrunken or receding gums, comprising the steps of:

applying a mixture of from 10 to 90 percent by volume dry powdered alum and from 90 to 10 percent by volume dry powdered cloves to the gums;

allowing the mouth to drain for 1 to 2 minutes;

rinsing the gums and mouth with fresh water; and repeating the foregoing steps at least daily until the gums return to normal.

4. A method as claimed in claim 3, wherein the alum and cloves of the mixture are mixed in approximately equal proportions by volume.

5. A method as claimed in claim 3, wherein the steps are performed 2 or 3 times a day.

6. A method for making a preparation for treating pyorrhea and other gum diseases which result in symptoms of swollen, bleeding, sensitive, shrunken or receding gums, comprising the steps of:

drying alum and whole cloves at 180° to 200° F. for 8 to 10 hours;

allowing the dried alum and dried cloves to cool to room temperature in a dry environment;

crushing the dried alum and dried cloves to a powder; and mixing the dry powdered alum and cloves in a volume ratio of from 1 to 9 parts alum and from 9 to 1 parts cloves.

7. A method as claimed in claim 6, wherein the cloves are dried at approximately 250° F. for 4 to 6 hours.

* * * * *